United States Patent [19]
Fry

[11] Patent Number: 5,477,849
[45] Date of Patent: Dec. 26, 1995

[54] SPACER FOR MEDICATION INHALER

[76] Inventor: Stephen Fry, 5206 E. Via Buena Vista, Paradise Valley, Ariz. 85253

[21] Appl. No.: 251,502

[22] Filed: May 31, 1994

[51] Int. Cl.⁶ .................................................. A61M 11/00
[52] U.S. Cl. ................................. 128/200.14; 128/200.23
[58] Field of Search ........................ 128/200.14, 200.23, 128/202.27

[56] References Cited

U.S. PATENT DOCUMENTS

| | | | |
|---|---|---|---|
| 1,263,079 | 4/1918 | Leon | 239/338 |
| 2,788,784 | 4/1957 | Birch | 128/200.23 |
| 3,486,730 | 12/1969 | Potash | 128/202.27 |
| 3,994,521 | 11/1976 | Hansen | 292/319 |
| 4,039,076 | 9/1977 | Murphy | 206/219 |
| 4,253,468 | 3/1981 | Lehmbeck | 128/726 |
| 4,470,412 | 9/1984 | Nowacki et al. | 128/200.18 |
| 4,484,577 | 11/1984 | Sackner et al. | 128/203.28 |
| 4,603,833 | 8/1986 | Christianson | 128/202.27 |
| 4,637,528 | 1/1987 | Wachinski et al. | 128/200.23 |
| 4,641,644 | 2/1987 | Andersson et al. | 128/200.23 |
| 4,690,332 | 9/1987 | Hughes | 239/338 |
| 4,706,663 | 11/1987 | Makiej | 128/200.23 |
| 4,739,754 | 4/1988 | Shaner | 128/203.15 |
| 4,793,342 | 12/1988 | Haber et al. | 128/202.27 |
| 4,827,921 | 5/1989 | Rugheimer | 128/202.27 |
| 4,841,953 | 6/1989 | Dobrill | 128/202.27 |
| 4,846,168 | 7/1989 | Abiko | 128/203.15 |
| 4,926,852 | 5/1990 | Zoltan | 128/200.23 |
| 4,953,545 | 9/1990 | McCarty | 128/200.23 |
| 5,161,524 | 11/1992 | Evans | 128/203.15 |
| 5,178,138 | 1/1993 | Walstrom | 128/200.23 |
| 5,203,323 | 4/1993 | Tritle | 128/200.23 |
| 5,239,993 | 8/1993 | Evans | 128/203.15 |

OTHER PUBLICATIONS

Advances in Therapy, vol. 10, No. 5, Sep./Oct. 1993, p: 209.

Primary Examiner—Aaron J. Lewis
Attorney, Agent, or Firm—LaValle D. Ptak

[57] ABSTRACT

A universal asthma and emphysema medication inhaler spacer comprises a cylindrical open-ended elongated chamber having a circular opening in the inlet end of a predetermined diameter and a predetermined depth. The outlet end of the chamber has an opening in it shaped to accommodate a human mouth. At the inlet end, the opening has opposed relief offsets on opposite sides to accommodate medication dispensers which have outlets of non-circular cross-sectional shapes, as well as circular shapes.

18 Claims, 1 Drawing Sheet

SPACER FOR MEDICATION INHALER

BACKGROUND

Relatively large numbers of persons suffer from a variety of respiratory diseases. Three main respiratory diseases are bronchitis, emphysema and asthma. In two of these, the airways of the lungs become constricted and breathing becomes labored or difficult. To some extent, the conditions caused by bronchitis and asthma are reversible. Inhaled medications have been developed to provide fairly rapid relief from the symptoms of bronchitis, emphysema and asthma. These medications typically are dispensed from hand-held, metered multi-dose inhalers, which deliver medications for dilating the airways of the lungs and/or for reducing the swelling of inflammatory allergic tissues of the airways. Such medications are sold under a number of different brand names.

Most hand-held inhalers include a pressurized aerosol container for the medication. The container then has a metered pressure-actuated outlet on it, which is coupled with an atomizer nozzle. The atomizer nozzle, in turn, directs the atomized medication spray into a mouthpiece, from which the medication is sprayed into the mouth of the user for inhalation into the lungs.

Almost all of the hand-held dispensers utilize the same operating principle described above, and are subject to the same limitations. A primary problem is that the medication is sprayed into the mouthpiece at a relatively high velocity and in a fairly narrow concentrated stream. A major percentage of the medication, which is sprayed through such a dispenser, is deposited in the mouth, throat and trachea of the user. Eventually, this deposited medication is swallowed; but such medication deposits do not reach the lungs where the medication is required. Consequently such deposited medication serves no medical purpose to the patient, and may additionally result in undesirable side effects and expense.

Since only a relatively small percentage of the overall medication which is released in a conventional hand-held, metered dose inhaler is applied to the airways and the lungs, more frequent application of medication is required. This, in turn, compounds the undesirable side effects of the deposited medication mentioned above. These problems are particularly aggravated for children and the elderly, who may have difficulty in coordinating the release of the medication and inhalation for most effective use.

Efforts have been made to improve the effectiveness of metered dose inhalers by providing a spacer between the standard mouthpiece of the inhaler, as sold, and the mouth of a user. Such devices are shown in the U.S. patents to Zoltan U.S. Pat. No. 4,926,852 and Walstrom U.S. Pat. No. 5,178,138. Both of these patents are directed to delivery devices in which a metered dose inhaler canister itself is inserted into a receptacle, which causes the dose to be directed away from the mouth of the user into a chamber, from which the aerosol spray is withdrawn by the user in a direction opposite to the direction the dosage is sprayed into the chamber.

The structure disclosed in the Zoltan patent is the simpler structure of these two delivery devices. In Zoltan, to permit air to be drawn through the spacer and out through the mouthpiece, air inlets are provided in the end of the spacer opposite from the end in which the medication is admitted. This is done by a series of small perforations and by means of a generally truncated cone, which helps to baffle the sprayed agent and to mix the agent with air which is admitted into the chamber when a patient withdraws air from the mouthpiece. In both of these devices, the medication canister itself is removed from the remainder of the inhaler devices, which are normally sold as a unit with the canisters. The devices of both Walstrom and Zoltan are relatively complex in configuration, and require incorporation of an atomizer nozzle as part of their construction. Thus, the atomizer nozzle which normally is supplied with the mouthpiece of the metered dose inhaler is wasted or discarded.

Two other types of spacers, which do not require an atomizer nozzle and which operate in line with the conventional mouthpiece of a standard metered dose inhaler, are described in the U.S. Pat. Nos. 4,470,412 and 4,953,545. The devices of both of these patents operate in a similar manner; although the one disclosed in U.S. Pat. No. 4,953,545 is of a simpler configuration than the device disclosed in the '412 patent. The devices of both of these patents are in the form of elongated cylindrical chambers. In patent '545 the device is simply a hollow canister; while the device of patent No. '412 includes additional features, such as a filter and a whistle in the multiple part assembly. To accommodate the mouthpiece end of different types or shapes of dispensers, both of these devices have the inlet end closed with a resilient plastic material having an aperture in the center of it. The material of the aperture is made sufficiently soft to stretch and conform around the shape of different inhaler mouthpieces. Consequently, in constructing the devices of both of these patents, the provision of the resilient aperture for receiving the various shaped mouthpieces means that this portion of the device must be made of a different material from the more rigid canister forming the main body of the spacer. As a consequence, this part needs to be separately manufactured and installed. This results in increased manufacturing costs. In addition, the resiliency of the aperture end of these devices permits misalignment of the mouthpiece, which could direct medication onto the wall of the spacer instead of into the center of the spacer chamber. This would waste the medication.

Another spacer for metered dose inhalers is disclosed in "Advances in Therapy", Vol. 10, No. 5, Sept/Oct 1993, on Page 209. The device disclosed in this article is a generally circular shaped housing which accommodates a pressurized aerosol canister at one side. The aerosol canister or dispenser must be removed from the atomizer and mouthpiece with which it normally is sold, and inserted into the spacer device. As a consequence, the spacer requires the inclusion of an atomizer in it. This nozzle is inserted between two polypropylene shells which, in turn, shape the round expansion chamber. Upon actuation and prior to inspiration from a mouthpiece opening opposite the diffuser nozzle, the emitted particulate stream is forced into a spiral. The expansion chamber creates a whirling flow of expelled particles, which are intended to remain suspended long enough to expend their kinetic energy.

Other spacers, specifically directed to a particular type of device with which they are used, are disclosed in the U.S. patents to Hansen U.S. Pat. No. 3,994,521; Lehmbeck U.S. Pat. No. 4,253,468; and Tritle U.S. Pat. No. 5,203,323. None of the devices disclosed in these three patents are directed to any type of "universal" accommodation for the mouthpiece portion of an otherwise standard inhaler to accommodate different shapes of mouthpieces. All of these devices are relatively complex in configuration.

It is desirable to provide an inhaler spacer which is capable of use with different shaped mouthpiece portions of commercial, standard inhalers, which is simple in configuration, compact easy to use, and relatively inexpensive.

SUMMARY OF THE INVENTION

It is an object of this invention to provide an improved spacer for medication delivery devices.

It is another object of this invention to provide a universal spacer for aerosol inhalers.

It is an additional object of this invention to provide an improved spacer for use with metered dose inhalers having different mouthpiece shapes.

It is a further object of this invention to provide an improved spacer for an aerosol metered dose inhaler, which is of simple construction, compact is easy to use, and is easy to clean.

In accordance with a preferred embodiment of this invention, a medication delivery device includes an elongated chamber. This chamber has an open inlet end and an open outlet end, with the outlet end being shaped to accommodate a human mouth. The open inlet end of the chamber has a substantially circular opening in it. This circular opening has a predetermined diameter and a predetermined depth. The circular opening also includes opposed relief offsets on opposite sides to accommodate medication dispensers having outlets with non-circular cross-sectional shapes, as well as circular cross-sectional shapes.

DETAILED DESCRIPTION

Figure 1:
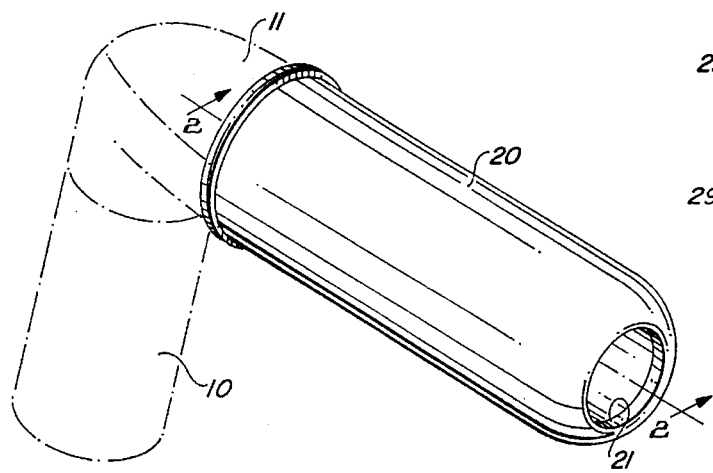
FIG. 1 is a front perspective view of a preferred embodiment of the invention.

Reference now should be made to the drawing, in which the same reference numbers are used throughout the different figures to designate the same components. FIG. 1 is a front perspective view of a spacer 20, in accordance with a preferred embodiment of this invention. The spacer 20 is used with a metered dose inhaler 10, which is depicted in dotted lines. The dispenser 20 has an inwardly turned right-hand outlet end with a circular opening 21 in it. The outer diameter of the spacer 20 is approximately one and one-fourth inches; and the diameter of the opening 21 is approximately one-half inch. This permits the opening 21 readily to accommodate a human mouth for inhaling aerosol medication located within the body of the spacer 20. The overall length of the spacer 20 is approximately three and one-fourth inches for a typical commercial application.

Figure 2:
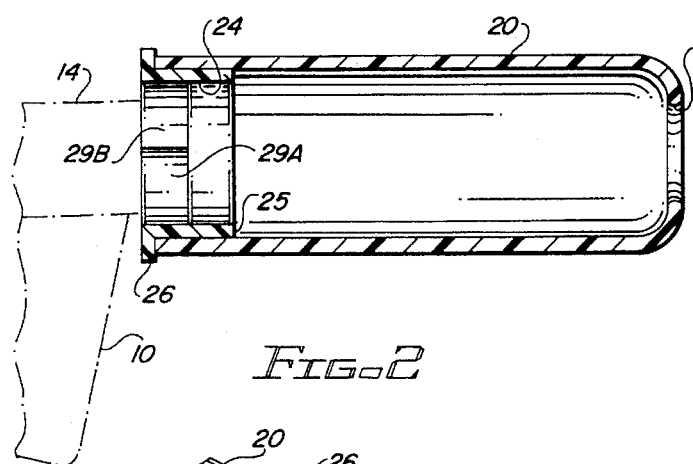
FIG. 2 is a cross-sectional view taken along the line 2—2 of FIG. 1.

As illustrated in FIG. 2, the spacer 20 also is open at its left-hand or inlet end to accommodate a separate inlet end cap 25, which is inserted into the left-hand open end of the cylindrical spacer 20 with a friction fit. An outwardly directed flange 26 limits the extent of insertion of the inlet end cap 25 into the spacer, as illustrated in FIG. 2. Also as is most readily apparent from an examination of FIGS. 2 and 3, the end cap 25/26 has a circular opening 24 extending through it. This opening has a diameter which is less than the internal diameter of the cylinder 20 by the amount of the wall thickness of the cap 25, which extends into the hollow elongated cylindrical chamber 20. The circular opening 24 has its center located on the central longitudinal axis of the cylindrical chamber 20.

Figure 3:
FIG. 3 is an enlarged perspective view of a portion of the embodiment shown in FIGS. 1 and 2.
Figure 4:
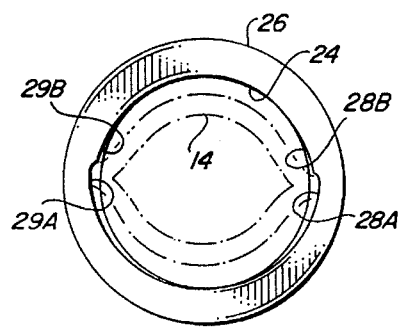
FIGS. 4, 5, 6 and 7 are end views of the portion shown in FIG. 3 illustrating use with aerosol delivery devices having different mouthpiece configurations.
Figure 5:
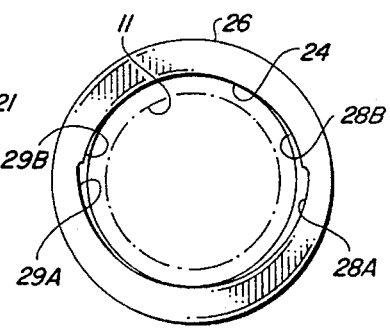

As shown most clearly in FIGS. 3 through 7, the circular opening 24 is shaped to accommodate the external diameter of a standard circular mouthpiece 11 (as shown in FIGS. 1 and 5) of a popular brand of metered dose inhaler currently available on the market. When the mouthpiece end 11 of the inhaler is inserted into the inlet opening 24, a friction fit between the inner wall of the circular opening 24 with the outer wall of the mouthpiece portion 11 takes place. This friction fit causes the mouthpiece 11 of the inhaler to be centered on the axis of the chamber 20. In this position, the metered dose inhaler 10/11 then may be used to dispel a metered dose of inhalant through the spray nozzle included in the delivery system of the metered dose inhaler 10/11. The length of the chamber 20 is selected to permit the particles of medication to be mixed with air drawn into the chamber when the used inhales through the opening 21, such air being pulled around the exterior of the mouthpiece 11 through slight differences in the opening 24 and the outer diameter of the circular mouthpiece 11. This causes the size of the particles released at the mouthpiece or outlet end 21 of the chamber 20 to be significantly reduced in size from those released at the inlet end 25/26; so that there is an increased potential that the medication will be carried into the airways and lungs of the user, reducing loss of medication by impaction on the inner walls of the spacer 20 and the mouth and tongue of the user.

The chamber 20 and the inlet end cap 25/26 preferably are made of rigid clear plastic material, such as polypropylene or the like. As illustrated in FIG. 2, these parts are shown as made in two portions, namely the cylindrical chamber 20 with the mouthpiece or outlet end 21, and the inlet end cap 25/26. The entire assembly, however, could be manufactured as a single integral unit, if desired. Whether the device is made of two parts, as shown in FIG. 2, or is made in one piece as an integral unit, cleaning is greatly facilitated. There are no soft surfaces or sharp corners where unused medication or other materials can become lodged. In addition, because of the shape and types of materials which are employed, it is easy to clean the spacer in a dishwasher, if desired. It is important for the spacer to be easily cleaned; so that reuse of the spacer is possible without exposing the user to bacterial and viral infections which may possibly breed in a spacer if it is not regularly cleaned. By making the spacer easy to clean, the likelihood that it will be cleaned between uses is greatly increased.

Figure 6:
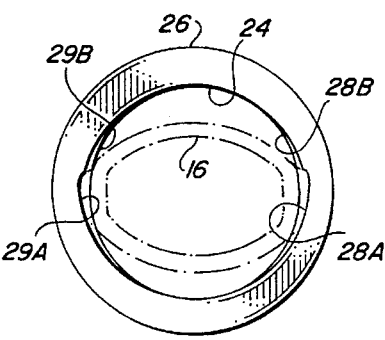
Figure 7:
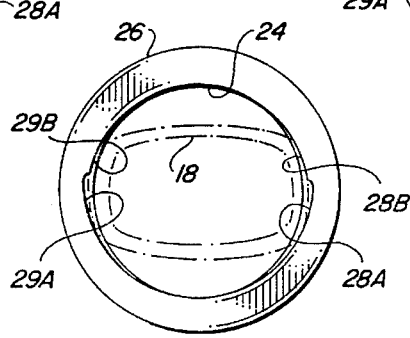

As illustrated in FIGS. 4, 6 and 7, other common metered dose inhaler dispensers currently on the market employ mouthpiece end configurations which are not the full circle 11, which has been illustrated in FIG. 5 and described above. Three other shapes, 14, 16 and 18, are currently in common use. To accommodate these other shapes, the inlet end 25/26 of the device shown in FIGS. 1 through 3 is provided with a pair of spaced relief areas, generally in the form of substantially V-shaped notches or indentations located on opposite sides of the circular opening 24.

As illustrated in FIGS. 3 through 7, these relief areas comprise an area consisting of two portions 28A and 28B on the right-hand side (as viewed in all of FIGS. 3 through 7) and a corresponding relief area 29A/29B on the left-hand side (again, as shown in all of FIGS. 3 through 7). These relief areas extend approximately half way into the full depth of the circular opening 24 in the end cap 25/26, as shown most clearly in FIGS. 2 and 3. As a consequence, when the flattened oval mouthpiece 14 of a dispenser such as used on the TILADE® (neocromil sodium) inhaler is used, the pointed edges of the somewhat flattened oval shape of the mouthpiece fit into the intersection points of the two relief areas 28A/28B and 29A/29B, as illustrated in FIG. 4. The opposing corners of the flattened oval mouthpiece 14 then rest against the shoulder formed by the remaining unrelieved portion of the circular opening 24 to frictionally hold the mouthpiece 14 centered in place in the end cap 25/26.

Similarly, another generally oval shaped mouthpiece end, with straight edges on each side of the oval, such as the mouthpiece 16 used in the ATROVENT® (ipratropium bromide) inhaler has exterior dimensions such that the mouthpiece 16 may be fully extended into the opening 24, with the corners or edges of the mouthpiece 16 frictionally engaging the circular portion 24 of the spacer to permit the use of an Atrovent® metered dose inhaler. The rigid opening 24 centers the mouthpiece 16 on the axis of the chamber 20. As is readily apparent from an examination of both FIGS. 4 and 6, when either of the TILADE® or ATROVENT® inhalers are used, air is drawn into the chamber 20 from around the mouthpiece 14 or 16 to mix with the medication as the user inhales through the opening 21 of the spacer.

Another type of mouthpiece, which is similar in overall shape to the one described above in conjunction with FIG. 6, is employed by the PROVENTIL® (albuterol) aerosol metered dose inhaler. The PROVENTIL® mouthpiece 18 is shown in FIG. 7, and is generally of the same overall shape as the mouthpiece 16 of the Atrovent® inhaler, but is somewhat larger in size; so that it fits into the relief areas 28A/28B and 29A/29B, as shown in FIG. 7, to abut against the shoulder formed by these relief areas with the inner part of the circular opening 24 illustrated in FIG. 3. Once again, air is drawn into the chamber 20 by a person inhaling through the opening 21 as the aerosol medication is dispensed into the chamber in the manner described above.

It has been found that by configuring the end cap 25/26 with the relief areas 28A/28B and 29A/29B as described above, all of the different commercially available metered dose inhalers, such as the ones described above, may be universally used with the spacer 20. Since no flexible plastic material is required in the construction of the device, the same rigid polypropylene plastic is used for all parts of the spacer, which facilitates manufacture, assembly and cleaning of the device throughout its use. A typical inside diameter of the circular opening 24 is 15/16 inches, with the distance between the inner points of the V-shaped bottoms of the relief areas 28A/28B and 29A/29B being 1 1/16 inches to frictionally accommodate the TILADE® dispenser. The other dispenser mouthpieces 16 and 18, which have been shown in conjunction with FIGS. 6 and 7, are accommodated by these dimensions. It should be noted that all of the dispensers have relatively rigid mouthpieces, but are made of plastic which has some resilience in it; so that the friction fits which have been described above may be effected.

The foregoing description of the preferred embodiment of the invention is to be considered as illustrative and not as limiting. Various changes and modifications will occur to those skilled in the art for performing substantially the same function, in substantially the same way, to achieve substantially the same result, without departing from the true scope of the invention as defined in the appended claims.

I claim:

1. A medication delivery device including in combination:
    an elongated chamber made of rigid material and having an open inlet end and an open outlet end, said outlet end being shaped to accommodate a human mouth; and
    said open inlet end of said chamber having a substantially circular opening therein with a predetermined diameter and a predetermined depth for accommodating a medication dispenser having an outlet with a circular cross-sectional shape; said circular opening further including opposed rigid relief offsets on opposite sides thereof to accommodate medication dispensers having outlets with non-circular cross-sectional shapes.

2. The combination according to claim 1 wherein said chamber is made of plastic.

3. The combination according to claim 2 wherein said chamber is a cylindrical chamber having an internal diameter greater than said predetermined diameter.

4. The combination according to claim 3 wherein said elongated cylindrical chamber has a longitudinal central axis and at least said circular opening at the inlet end of said chamber is centered on said axis.

5. The combination according to claim 1 wherein said chamber is a cylindrical chamber having an internal diameter greater than said predetermined diameter.

6. The combination according to claim 5 wherein said elongated cylindrical chamber has a longitudinal central axis and at least said circular opening at the inlet end of said chamber is centered on said axis.

7. A medication delivery device including in combination:
    an elongated chamber having an open inlet end and an open outlet end, said outlet end being shaped to accommodate a human mouth; and
    said open inlet end of said chamber having a substantially circular opening therein with a predetermined diameter and a predetermined depth for accommodating a medication dispenser having an outlet with a circular cross-sectional shape; said circular opening further including opposed relief offsets on opposite sides thereof extending from the inlet end thereof a distance less than said predetermined depth to accommodate medication dispensers having outlets with non-circular cross-sectional shapes.

8. The combination according to claim 7 wherein said relief offsets are located substantially 180° apart on opposite sides of said opening.

9. The combination according to claim 8 wherein said relief offsets are generally in the form of V-shaped cutouts which extend into said circular opening from the inlet end of said chamber a predetermined distance which is less than said predetermined depth.

10. The combination according to claim 9 wherein said chamber is made of first and second parts with said first part comprising an elongated cylindrical tube which is open at both ends, and said second part fits into the inlet end of said chamber and comprises a relatively short, hollow, cylindrical section having a substantially circular opening therein.

11. The combination according to claim 10 wherein said first and second sections slip fit together.

12. The combination according to claim 11 wherein said second section is inserted into the interior of said first section.

13. The combination according to claim 12 wherein the outlet end of said elongated chamber tapers inwardly to a circular opening in said outlet end which is of smaller diameter than the internal diameter of said chamber.

14. The combination according to claim 13 wherein said openings in said outlet and said inlet end of said chamber are aligned with the longitudinal axis of said chamber.

15. A medication delivery device including in combination:
    an elongated chamber comprising a first part in the form of an elongated cylindrical tube having an open inlet end and an open outlet end, and a relatively short, hollow, cylindrical second part having an inlet end and fitted into the inlet end of said first part, said outlet end of said first part being shaped to accommodate a human mouth; and said inlet end of said second part of said chamber having a substantially circular opening therein with a predetermined diameter and a predetermined depth for accommodating a medication dispenser having an outlet with a circular cross-sectional shape; said circular opening further including opposed relief offsets on opposite sides thereof to accommodate medication dispensers having outlets with non-circular cross-sectional shapes.

16. The combination according to claim 15 wherein said chamber is made of rigid material.

17. The combination according to claim 16 wherein said chamber is made of plastic.

18. The combination according to claim 17 wherein said first and second sections slip fit together.

* * * * *